(12) United States Patent
Benseghir et al.

(10) Patent No.: US 12,108,993 B2
(45) Date of Patent: Oct. 8, 2024

(54) METHODS AND SYSTEM FOR GUIDED DEVICE INSERTION DURING MEDICAL IMAGING

(71) Applicant: GE Precision Healthcare LLC, Milwaukee, WI (US)

(72) Inventors: Thomas Benseghir, Yvelines (FR); Selim Zenagui, Yvelines (FR); Maxime Taron, Hauts de Seine (FR); Yves Trousset, Palaiseau (FR); Raphael Doustaly, Rhône (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 61 days.

(21) Appl. No.: 17/444,535

(22) Filed: Aug. 5, 2021

(65) Prior Publication Data
US 2023/0045275 A1   Feb. 9, 2023

(51) Int. Cl.
A61B 34/20 (2016.01)
A61B 6/12 (2006.01)
A61B 34/10 (2016.01)
A61B 90/00 (2016.01)

(52) U.S. Cl.
CPC .............. *A61B 34/20* (2016.02); *A61B 6/12* (2013.01); *A61B 90/37* (2016.02); *A61B 2034/102* (2016.02); *A61B 2034/107* (2016.02); *A61B 2034/2065* (2016.02); *A61B 2090/376* (2016.02)

(58) Field of Classification Search
CPC ........... A61B 34/20; A61B 6/12; A61B 90/37; A61B 2034/102; A61B 2034/107; A61B 2034/2065; A61B 2090/376; A61B 34/10
See application file for complete search history.

(56) References Cited

U.S. PATENT DOCUMENTS

| 5,846,086 A | 12/1998 | Bizzi et al. |
| 7,505,616 B2 | 3/2009 | Zeineh |
| 7,559,935 B2 | 7/2009 | Solar et al. |
| 7,637,915 B2 | 12/2009 | Parmer et al. |

(Continued)

FOREIGN PATENT DOCUMENTS

| EP | 1925265 A1 * | 5/2008 | ............. A61B 90/36 |
| ES | 2778041 T3 * | 8/2020 | ......... A61B 17/3403 |

(Continued)

OTHER PUBLICATIONS

Mwikirize, C. et al., "Convolution neural networks for real-time needle detection and localization in 2D ultrasound," International Journal of Computer Assisted Radiology and Surgery, vol. 13, No. 5, May 2018, 11 pages.

(Continued)

*Primary Examiner* — Colin T. Sakamoto
*Assistant Examiner* — Tommy T Ly
(74) *Attorney, Agent, or Firm* — McCoy Russell LLP

(57) ABSTRACT

Various methods and systems are provided for medical imaging. In one embodiment, a method for an interventional imaging procedure comprises identifying a medical device during insertion of the medical device within a subject based on live images of the insertion, extrapolating a trajectory of the medical device during the insertion in real-time based on the live images of the insertion, and displaying the extrapolated trajectory of the medical device on the live images.

19 Claims, 5 Drawing Sheets

(56) References Cited

U.S. PATENT DOCUMENTS

| | | | |
|---|---|---|---|
| 7,658,879 B2 | 2/2010 | Solar | |
| 7,699,854 B2 | 4/2010 | Mazzocchi et al. | |
| 7,896,889 B2 | 3/2011 | Mazzocchi et al. | |
| 7,916,913 B2 | 3/2011 | Zeineh | |
| 7,981,120 B2 | 7/2011 | Mazzocchi et al. | |
| 8,747,419 B2 | 6/2014 | Solar et al. | |
| 8,843,235 B2 | 9/2014 | Ota et al. | |
| 9,147,261 B2 | 9/2015 | Dogra et al. | |
| 9,387,008 B2 | 7/2016 | Sarvestani et al. | |
| 9,445,793 B2 | 9/2016 | Solar et al. | |
| 9,488,710 B2 | 11/2016 | Boada et al. | |
| 9,778,275 B2 | 10/2017 | Mellars | |
| D824,027 S | 7/2018 | Flores et al. | |
| 10,408,910 B2 | 9/2019 | Cauley et al. | |
| 10,456,103 B2 | 10/2019 | Bose et al. | |
| 10,456,201 B1 | 10/2019 | Solar et al. | |
| 10,466,321 B2 | 11/2019 | Cohen | |
| 10,751,023 B2 | 8/2020 | Bose et al. | |
| 10,775,467 B2 | 9/2020 | Heidemann et al. | |
| 10,904,114 B2 | 1/2021 | Thampy et al. | |
| 10,969,450 B2 | 4/2021 | Shi et al. | |
| 2009/0149867 A1* | 6/2009 | Glozman | A61B 34/70 600/407 |
| 2012/0065481 A1* | 3/2012 | Hunter | A61B 6/463 600/513 |
| 2013/0211244 A1* | 8/2013 | Nathaniel | A61B 34/20 600/424 |
| 2013/0345718 A1* | 12/2013 | Crawford | A61B 17/8866 606/130 |
| 2017/0119956 A1* | 5/2017 | Leeflang | A61M 5/1407 |
| 2017/0172662 A1* | 6/2017 | Panescu | A61B 34/37 |
| 2019/0320878 A1* | 10/2019 | Duindam | G06T 7/11 |
| 2020/0330159 A1* | 10/2020 | Zhang | G06T 1/0014 |
| 2021/0085268 A1* | 3/2021 | Alexandroni | A61B 90/39 |

FOREIGN PATENT DOCUMENTS

| | | | |
|---|---|---|---|
| WO | WO-2022035584 A1 * | 2/2022 | |
| WO | WO-2022229916 A1 * | 11/2022 | |

OTHER PUBLICATIONS

Pourtaherian, A., "Robust needle detection and visualization for 3D ultrasound image-guided interventions," Doctor of Philosophy, School of Electrical Engineering, Technische Universitat Eindhoven, Sep. 26, 2018, 209 pages.

Dorileo, E., "Needle modeling, insertion planning and steering for CT or MR image-guided robot-driven percutaneous procedures," HAL Archives, No. tel-02059022, Mar. 6, 2019, 116 pages.

* cited by examiner

METHODS AND SYSTEM FOR GUIDED DEVICE INSERTION DURING MEDICAL IMAGING

FIELD

Embodiments of the subject matter disclosed herein relate to medical imaging, and more particularly, to x-ray fluoroscopic imaging.

BACKGROUND

Non-invasive imaging technologies allow images of the internal structures or features of a patient or object to be obtained without performing an invasive procedure on the patient or object. In particular, such non-invasive imaging technologies rely on various physical principles, such as the differential transmission of x-rays through the target volume or the reflection of acoustic waves, to acquire data and to construct images or otherwise represent the observed internal features of the patient or object.

For example, in fluoroscopy and other x-ray based imaging technologies such as computed tomography (CT), x-ray radiation is directed toward a subject, typically a patient in a medical diagnostic application, a package or baggage in a security screening application, or a fabricated component in an industrial quality control or inspection application. A portion of the radiation impacts a detector where the image data is collected and used in an image generation process. In the images produced by such systems, it may be possible to identify and examine the internal structures and organs within a patient's body, objects within a package or container, or defects (e.g., cracks) within a fabricated component.

In certain contexts, such as fluoroscopy applications used in support of interventional or navigation procedures, x-rays may be acquired at a high frame rate over an extended period to provide real-time image data that may be used to guide or navigate a tool within a patient. In complement, cone beam computed tomography (CBCT) may be used in interventional x-ray guided needle procedures, preoperative three-dimensional (3D) imaging, and or intraoperative 3D imaging.

BRIEF DESCRIPTION

In one aspect, a method for an interventional imaging procedure includes identifying a medical device during insertion of the medical device within a subject based on live images of the insertion, extrapolating a trajectory of the medical device during the insertion in real-time based on the live images of the insertion, and displaying the extrapolated trajectory of the medical device on the live images. In this way, the medical device (e.g., a needle) may be inserted with increased accuracy and decreased operator effort.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
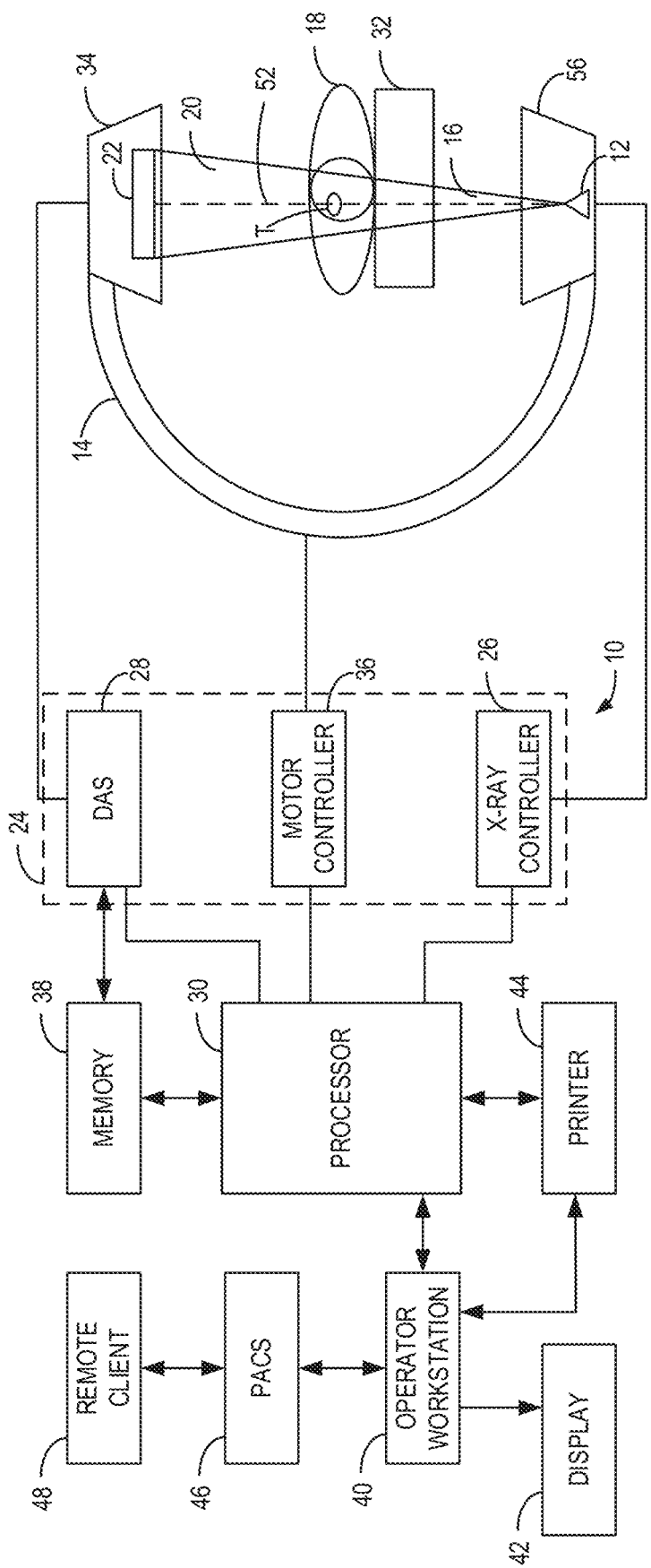
FIG. 1 shows a pictorial view of an imaging system, according to an embodiment.

Embodiments of the present disclosure will now be described, by way of example, with reference to the FIGS. 1-5, which relate to various embodiments for providing an augmented trajectory of a medical device in real-time during insertion of the medical device via real-time medical imaging. During an interventional imaging procedure, such as a surgical procedure monitored/assisted by fluoroscopic imaging, continuous, real-time x-ray images of a patient may be displayed, allowing clinicians to monitor movement of an inserted medical device (also simply termed "device" herein), such as a needle, surgical tool, or scope, relative to anatomical features. The acquired x-ray images are two-dimensional (2D) conic projections.

In some procedures, a three-dimensional (3D) model may be generated and overlaid on the live 2D x-ray images. The 3D model may provide a guided workflow for insertion of the medical device. For example, the 3D model may indicate an entry point and pathway for inserting the medical device to a target location (e.g., an anatomical region or structure). While the guided workflow may anticipate the positioning of the medical device according to the procedure being performed and inherent insertion characteristics of the medical device, the guided workflow does not anticipate or adapt for deviations of the medical device from the proposed entry point and pathway. Further, the guided workflow does not provide real-time feedback to the clinician performing the insertion regarding their actual trajectory within the patient. For example, even with the guided workflow, precise positioning of the medical device may be challenging. Starting from the puncture site on the patient, it may be difficult for the clinician to anticipate if an angulation taken by the medical device will reach the target location. Additionally, respiratory motion of the patient may further complicate precise positioning. This may be especially challenging during the insertion of flexible devices that may deform and deflect during the puncture.

Therefore, according to embodiments disclosed herein, a virtual estimated trajectory of the device during the procedure, from the puncture to the target location, may provide feedback and additional guidance to the clinician. For example, the real-time x-ray images may be automatically analyzed in real-time to identify the medical device, such as via segmentation, and extrapolate the trajectory in the patient. The extrapolation may take into account a location of a distal portion of the medical device, characteristics of the medical device (such as length, thickness, shape, stiffness or flexibility, etc.), and the type of procedure being performed, for example.

By providing a real-time virtual trajectory of the medical device, the medical device may be accurately placed more easily and more quickly, reducing an amount of time it takes to perform the procedure and reducing its difficulty as well as potential complications. As a result, the clinician may be able to perform more procedures in a given day. Further, patient comfort may be increased by decreasing the procedure time. Further still, a radiation dose provided to the patient may be decreased due to the shortened imaging duration.

Figure 2:
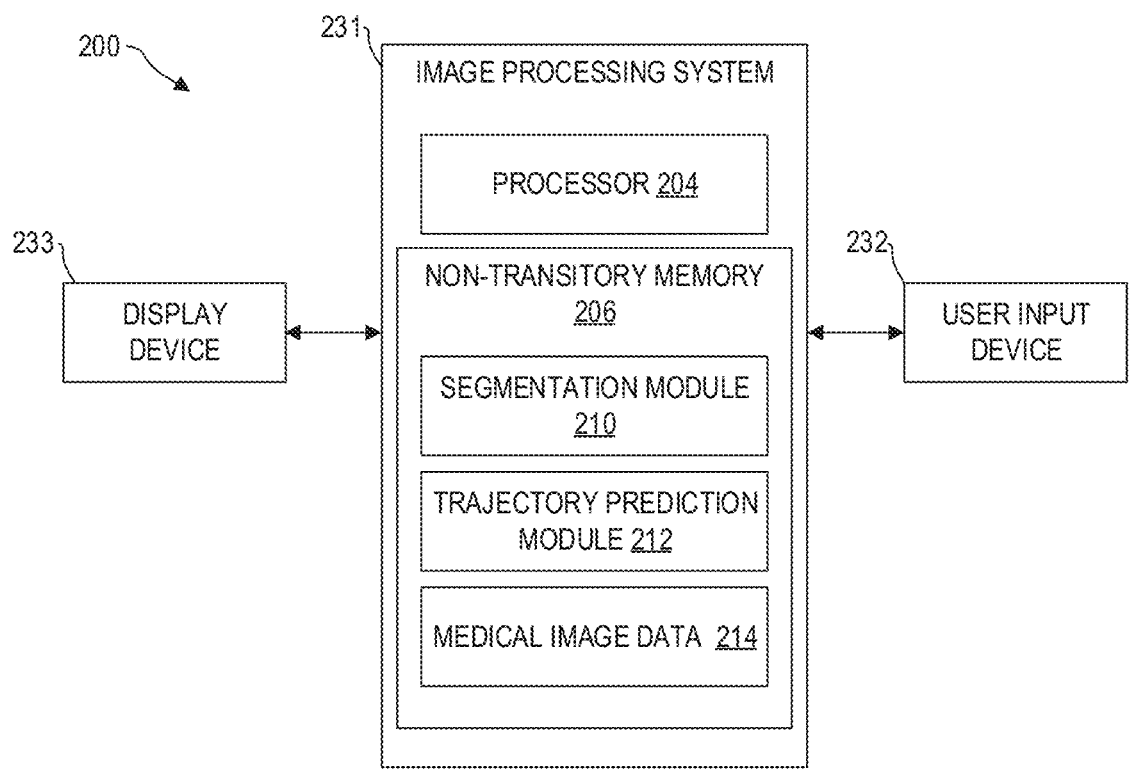
FIG. 2 shows a block diagram of an exemplary image processing system for segmenting and analyzing images, according to an embodiment.
Figure 4:
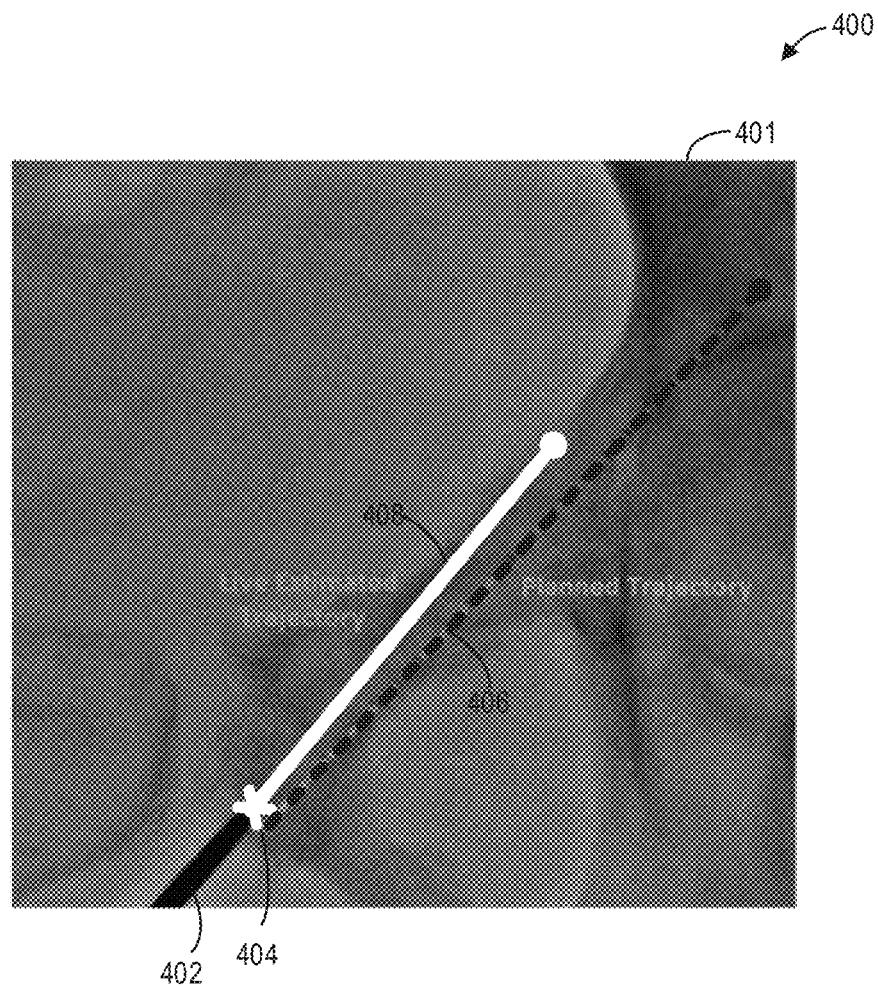
FIG. 4 shows a first example of displaying a live estimated trajectory of a device during insertion.
Figure 5:
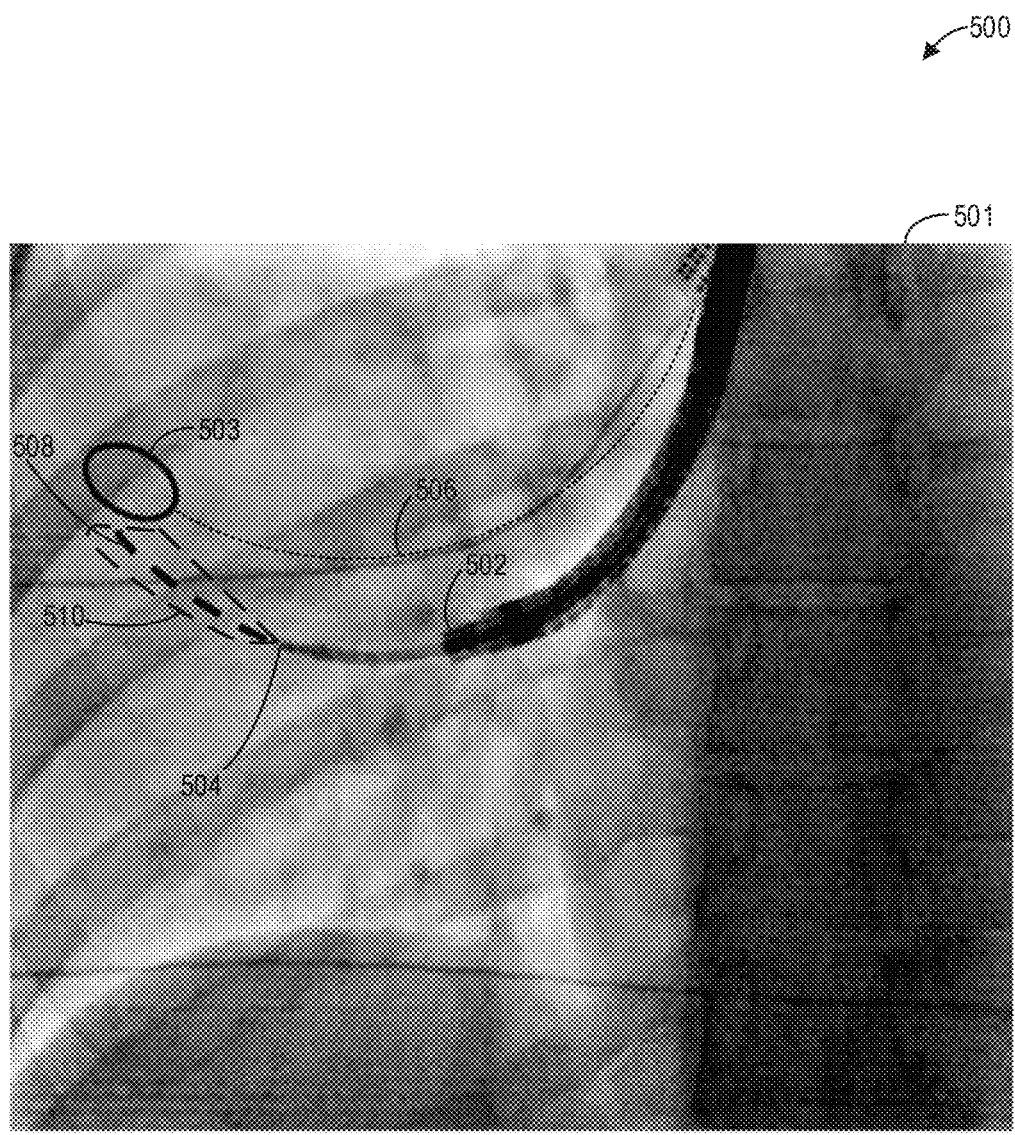
FIG. 5 shows a second example of displaying a live estimated trajectory of a device during insertion, according to an embodiment.

An example of a projection imaging system that may be used to acquire medical images of a region of interest is shown in FIG. 1. An example image processing system that may be used to determine a real-time trajectory of a device (e.g., a needle) based on live images acquired during insertion of the device is shown in FIG. 2. The image processing system may employ image processing algorithms to segment the device, localize the device, and extrapolate the trajectory of the device according to the method shown in FIG. 3. FIGS. 4 and 5 provide examples of displaying a real-time trajectory of a needle on real-time medical images.

Turning now to the figures, FIG. 1 illustrates diagrammatically an exemplary embodiment of an imaging system 10 for acquiring and processing image data. In the illustrated embodiment, imaging system 10 is a digital x-ray system designed both to acquire original image data and to process the image data for display. The imaging system 10 may be a stationary or mobile x-ray system. In the embodiment illustrated in FIG. 1, the imaging system 10 is depicted as a C-arm fluoroscopic imaging system, yet it may be understood that other forms of imaging and/or navigation systems may be used within the scope of the present disclosure. For example, it may be understood that the present techniques may also be useful when applied to images acquired using other imaging modalities, such as standard, non-fluoroscopic x-ray imaging, tomosynthesis, and so forth. The present discussion of a fluoroscopic imaging modality is provided merely as an example of one suitable imaging modality. For example, the imaging system 10 may be any imaging system that acquires two-dimensional images (e.g., slices or projections) of three-dimensional objects.

The imaging system 10 may acquire x-ray attenuation data at a variety of views around a patient and suitable for tomographic reconstruction. The imaging system 10 includes an x-ray source 56 secured to a C-arm 14. The x-ray source 56 may exemplarily be an x-ray tube, a distributed x-ray source (such as a solid-state or thermionic x-ray source) or any other source of x-ray radiation suitable for the acquisition of medical or other images. The x-ray source 56 may also be referred to as a radiation source. For example, the x-ray source 56 may comprise an x-ray generator and x-ray tube. The x-ray source 56 emits x-ray radiation 16 from a focal spot 12 in the direction of a subject (or object) 18. For example, the subject 18 may be a patient. In the depicted embodiment, the x-ray radiation 16 is emitted in a cone shape, e.g., a cone-beam. This cone-beam of x-rays pass through an imaged volume of the subject 18. An incident portion (also referred to as incident x-rays) 20 of the x-ray radiation 16 passes through or around the subject 18 and impacts (or impinges on) an x-ray detector 34 including a detector array 22. The x-ray detector 34 may also be referred to as a radiation detector. In the present example, the x-ray detector 34 is a digital x-ray detector and may be portable or permanently mounted to the imaging system 10.

In certain embodiments, the detector array 22 may convert the incident x-ray photons to lower energy photons which are detected. Electrical signals are generated in response to the detected photons, and these signals are processed to reconstruct images of the features (e.g., anatomical features) within the subject 18. Together, the x-ray source 56 and the x-ray detector 34 comprise an x-ray imaging chain.

As an example, the detector array 22 may include one or more complementary metal oxide semiconductor (CMOS) light imager panels, each separately defining an array of detector elements (e.g., pixels). Each detector element produces an electrical signal that represents the intensity of the x-ray beam incident at the position of the detector element when the beam strikes the detector array 22. This signal may be digitized and sent to a monitor/display device for display.

The x-ray source 56 and the x-ray detector 34 are exemplarily controlled by a system controller 24 that provides both power and control signals for the operation of the imaging system 10. The system controller 24 may control the x-ray source 56 via an x-ray controller 26, which may be a component of the system controller 24. In such an embodiment, the x-ray controller 26 may be configured to provide power and timing signals to the x-ray source 56.

The x-ray detector 34 is further exemplarily connected to the system controller 24. The system controller 24 controls the acquisition of the signals generated in the x-ray detector 34 (e.g., by the detector array 22). In an exemplary embodiment, the system controller 24 acquires the signals generated by the detector array 22 using a data acquisition system (DAS) 28. The DAS 28 receives data collected by readout electronics of the x-ray detector 34. The DAS 28 may receive sampled analogue signals from the x-ray detector 34 and convert the data to digital signals for subsequent processing by a processor 30 discussed in further detail herein. Alternatively, in other embodiments, the analogue to digital conversion may be performed by circuitry provided on the x-ray detector 34 itself. The system controller 24 may also execute various signal processing and filtration functions with regard to the acquired image signals, such as, but not limited to, initial adjustment of dynamic ranges and interleaving of digital image data.

Further, the x-ray detector 34 includes or communicates with control circuitry in the system controller 24 that commands acquisition of the signals generated in the detector array 22. The x-ray detector 34 may communicate with the system controller 24 via any suitable wireless communication or through a cable or other mechanical connection. Alternatively, operational commands may be implemented within the x-ray detector 34 itself.

The system controller 24 is further operationally connected to the C-arm 14 as well as to a table 32 configured to support the subject 18. A motor controller 36 of the system controller 24 provides instructions and commands to mechanical components of the C-arm 14 and the table 32 to carry out linear and/or rotational movement thereof. The linear and/or rotational movement of the C-arm 14 enables the x-ray source 56 and the x-ray detector 34 to be rotated one or multiple turns about the subject 18, such as rotated primarily in an X-Y plane or angled with respect to the subject. The distance between the x-ray detector 34 and the x-ray source 56 may also be adjusted. Further, the table 32 supporting the subject 18 may be ordinately moved with respect to the movement of the C-arm 14 and/or planned movement of the C-arm 14 to position the patient within the imaging field of view of the imaging system 10. Thus, movement of the patient and/or components of the imaging system to adjust the imaging field of view may include one or both of movements of the C-arm 14 and the table 32.

In general, system controller 24 commands operation of the imaging system 10 (such as via the operation of the x-ray source 56, the x-ray detector 34, and positioning systems described above) to execute examination protocols and to process acquired data. For example, the system controller 24, via the systems and controllers noted above, may rotate a gantry supporting the x-ray source 56 and the x-ray detector 34 about an area of interest or target T so that x-ray attenuation data may be obtained at a variety of views relative to the target T. For example, a central axis 52 of the x-ray radiation 16 may be focused at the target T. In the present example, the system controller 24 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processor 30 for reconstruction of images. The processor 30 may be one or more conventional microprocessors. The data collected by the DAS 28 may be transmitted to the processor 30 directly or after storage in a memory 38. Any type of memory suitable for storing data might be utilized by the imaging system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below. One example of image reconstruction may include cone beam computed tomography (CBCT) wherein images acquired at multiple angles about the subject 18 are projected against each other to form voxels of a 3D representation of the imaged region. Other forms of image reconstruction, including but not limited to processing image data from the detector signal to produce clinically useful images, may be used.

The processor 30 may be configured to receive commands and scanning parameters from an operator via an operator workstation 40, typically equipped with a keyboard, touchscreen and/or other input devices. The operator may control the imaging system 10 via the operator workstation 40. Thus, the operator may observe the reconstructed images and/or otherwise operate the imaging system 10 using the operator workstation 40. For example, a display 42 coupled to the operator workstation 40 may be utilized to observe the reconstructed images and to control imaging. Additionally, the images also may be printed by a printer 44 which may be coupled to the operator workstation 40.

Further, the processor 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. The PACS 46 may in turn be coupled to a remote client 48, radiology department information system (RIS), hospital information system (HIS) or to an internal or external network, so that others at different locations may gain access to the raw or processed image data.

While the preceding discussion has described the various exemplary components of the imaging system 10 separately, these various components may be provided within a common platform or in interconnected platforms. For example, the processor 30, the memory 38, and the operator workstation 40 may be provided collectively as a general or special purpose computer or workstation configured to operate in accordance with the aspects of the present disclosure. In such embodiments, the general or special purpose computer may be provided as a separate component with respect to the data acquisition components of the imaging system 10 or may be provided in a common platform with such components. Likewise, the system controller 24 may be provided as part of such a computer or workstation or as part of a separate system dedicated to image acquisition.

The imaging system 10 as shown in FIG. 1 may also include a variety of alternative embodiments generally configured to meet the particular needs of certain applications. For example, the imaging system 10 may be a fixed system, a mobile system, or a mobile C-arm system where the x-ray detector 34 is either permanently mounted inside one end of the C-arm 14 or removable from the system. Further, the imaging system 10 may be a table and/or wall stand system in a fixed x-ray room where the x-ray detector 34 is either permanently mounted together with the system or portable. Alternatively, the imaging system 10 may be a mobile x-ray system with a portable x-ray detector. Such a portable x-ray detector may be further constructed with a detachable tether or cable used to connect the detector readout electronics to the data acquisition system of the scanner. When not in use, the portable x-ray detector may be detached from the scan station for storage or transfer. In practice, the imaging system 10 may be any suitable x-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth. Further still, while an example of a flat-panel detector was described above, a digital detector system including image intensifier and a video camera may be used to convert the incident x-rays 20 to a video signal.

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

As will be described in more detail below, the subject 18 may be imaged with the x-ray imaging chain, including the x-ray source 56 and the x-ray detector 34. Although not explicitly shown, it may be understood that the x-ray imaging chain may further include various lenses (e.g., a collimating lens and/or a focusing lens) and apertures. The x-ray imaging chain is positioned around the subject 18 at different angles that are chosen by an operator (e.g., a clinician). The subject 18 lays on the table 32, and the position of the table 32 may also change throughout the imaging. The acquired x-ray images are 2D conic projections, and the changes to the imaging chain and the position of the table 32 may enable the operator to see an anatomy of the subject 18 under different angles and magnification factors. For example, a workflow of the imaging procedure may include acquiring several image sequences, which may be used to diagnose and if necessary, intervene on the subject 18. An anatomical place of interest may be viewed in these different images in real-time, which may help guide needle insertions or other interventions.

Referring to FIG. 2, an example medical image processing system 200 is shown. In some embodiments, the medical image processing system 200 is incorporated into a medical imaging system, such as a fluoroscopic imaging system (e.g., the imaging system 10 of FIG. 1), a magnetic resonance imaging (MM) system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processing unit 231, a user input device 232, and a display device 233. For example, the image processing unit 231 may be operatively and/or communicatively coupled to the user input device 232 and the display device 233.

The image processing unit 231 includes a processor 204 configured to execute machine readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices in a cloud computing configuration. In some embodiments, the processor 204 may include other electronic components capable of carrying out processing functions, such as a digital signal processor, a field-programmable gate array (FPGA), or a graphic board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

The non-transitory memory 206 may store a segmentation module 210, a trajectory prediction module 212, and medical image data 214. The segmentation module 210 may include one or more machine learning models, such as deep learning networks, comprising a plurality of weights and biases, activation functions, loss functions, gradient descent algorithms, and instructions for implementing the one or more deep neural networks to process input medical images. For example, segmentation module 210 may store instructions for implementing a neural network. The segmentation module 210 may include trained and/or untrained neural networks and may further include training routines, or parameters (e.g., weights and biases), associated with one or more neural network models stored therein. In one example, the training routine may include instructions for receiving training data sets from the medical image data 214, which comprise sets of medical images, associated ground truth labels/images, and associated model outputs for use in training one or more of the machine learning models stored in the segmentation module 210. In some embodiments, the training routine may receive medical images, associated ground truth labels/images, and associated model outputs for use in training the one or more machine learning models from sources other than the medical image data 214, such as other image processing systems, the cloud, etc. In some embodiments, one or more aspects of the training routines may include remotely-accessible networked storage devices in a cloud computing configuration. Additionally or alternatively, in some embodiments, the training routines may be used to generate the segmentation module 210 offline and remote from the image processing system 200. In such embodiments, the training routines may not be included in the segmentation module 210 but may generate data stored in the segmentation module 210.

Similarly, the trajectory prediction module 212 may include one or more algorithms, including machine learning modules, and instructions for implementing the one or more algorithms for processing input medical images. In some embodiments, the trajectory prediction module 212 may additionally use data received from the segmentation module 210 and/or a user as inputs. As will be elaborated herein, the segmentation module 210 may be used to identify and segment an inserted medical device (e.g., a needle) within a subject during interventional medical imaging (e.g., live fluoroscopy), and the trajectory prediction module 212 may precisely localize a distal portion of the inserted medical device and estimate (e.g., extrapolate) its trajectory within the patient.

The non-transitory memory 206 further stores the medical image data 214. The medical image data 214 includes, for example, images captured by an x-ray imaging modality, such as fluoroscopic x-ray images, anatomical images captured by an MM system or a CT system, etc. In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration.

The image processing system 200 may further include the user input device 232. The user input device 232 may comprise one or more of a touchscreen, a keyboard, a mouse, a trackpad, a motion sensing camera, or other device configured to enable a user to interact with and manipulate data within the image processing unit 231. As an example, the user input device 232 may enable a user to annotate imaged structures, such as to indicate a target location for medical device insertion.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206.

It should be understood that the image processing system 200 shown in FIG. 2 is one non-limiting embodiment of an image processing system, and other imaging processing systems may include more, fewer, or different components without parting from the scope of this disclosure.

As mentioned above, an image processing system (e.g., the image processing system 200 of FIG. 2) may receive images acquired by, or may be included in, an imaging system (e.g., the imaging system 10 of FIG. 1). The image processing system may analyze and annotate the acquired images in real-time. For the purposes of this disclosure, the term "real-time" is defined to include an action that is performed without any intentional delay (e.g., substantially at the time of occurrence). For example, the imaging system may acquire images at a pre-determined frame rate, reconstruct the images for display, and display the reconstructed images in real-time, and the image processing system may also process the reconstructed images to identify a medical device being inserted, determine a trajectory of the medical device, and overlay the trajectory of the medical device on the displayed images in real-time.

Figure 3:
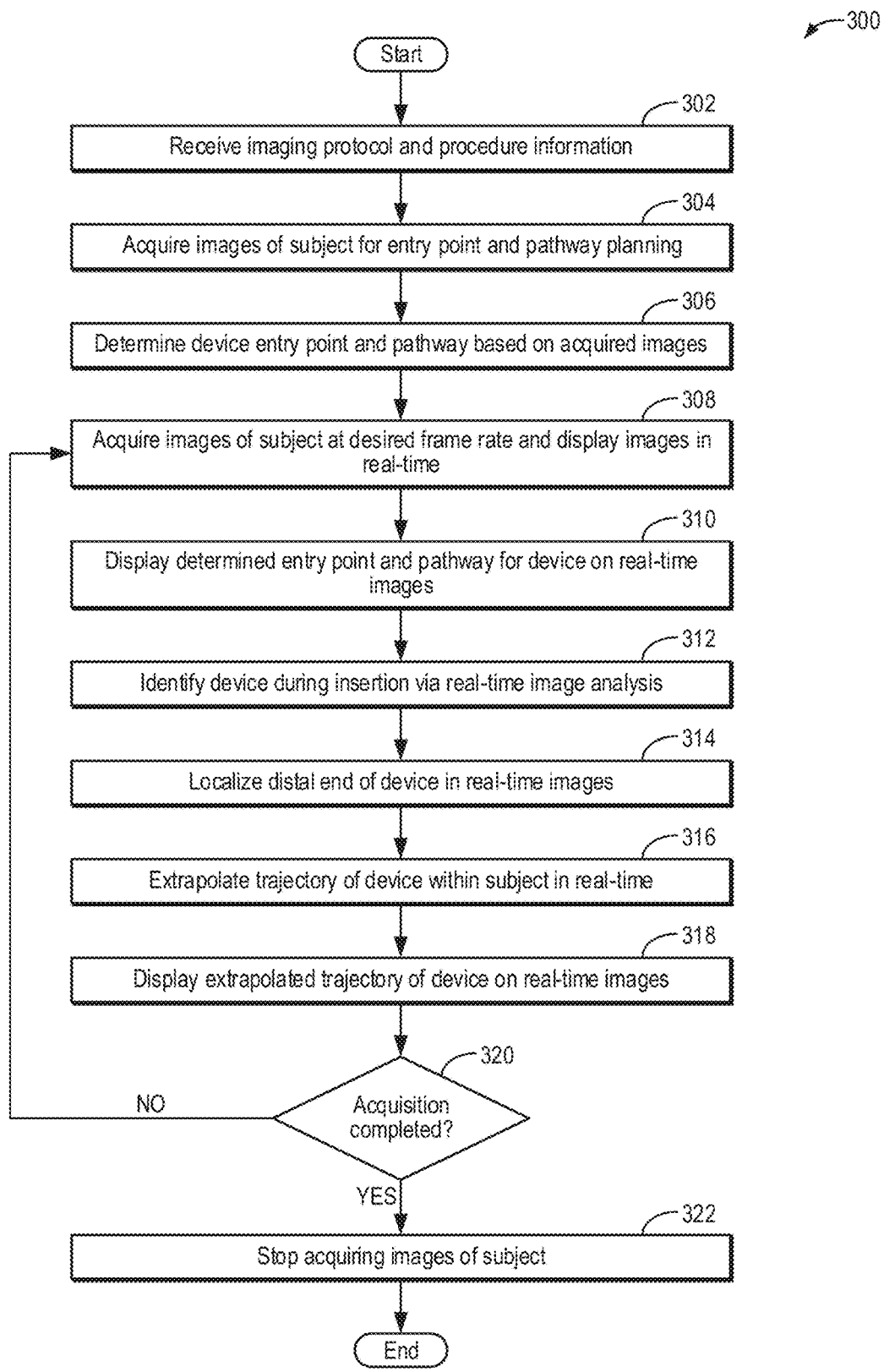
FIG. 3 is a flow chart illustrating a method for dynamic trajectory augmentation during an interventional imaging procedure, according to an embodiment.

In order to coordinate real-time imaging and image processing, FIG. 3 shows a method 300 for determining a medical device insertion trajectory and augmenting/annotating real-time images accordingly. The method will be described with regard to the systems and components described herein with respect to FIGS. 1-2, however it may be understood that the method may be implemented with other systems and components without departing from the scope of the present disclosure. The method 300 may be implemented as executable instructions in non-transitory memory of a computing device, such as the memory 38 of FIG. 1 and/or the non-transitory memory 208 of FIG. 2, and may be executed by one or more operatively connected processors, such as the processor 30 of FIG. 1 and/or the processor 204 of FIG. 2, in a coordinated manner. The method 300 will be described with respect to x-ray fluoroscopic imaging, although it may be understood that other imaging modalities may be used without departing from the scope of this disclosure.

At 302, the method 300 includes receiving imaging protocol and procedure information. For example, an operator of an imaging system (e.g., the imaging system 10 of FIG. 1) may input or select imaging protocol and procedure information, such as via an operator workstation (e.g., the operator workstation 40 of FIG. 1). The procedure information may include a type of interventional imaging procedure being performed and/or the imaging protocol for the procedure. For example, the procedure type or imaging protocol may specific the anatomy being imaged, prescribe a series of views to acquire (and the corresponding positions of imaging system to acquire the series of views), and indicate whether or not a contrast agent is used and its type. For example, the contrast agent may be administered to the subject in order to aid visualization of the anatomy of interest. As one example, the contrast agent may be injected in order to visualize vasculature. Illustrative examples of the procedure type include an endobronchial lung biopsy, a transjugular intrahepatic portosystemic shunt (TIPS) procedure, percutaneous tumor ablation, cancer treatment (such as using cryoablation, radiofrequency ablation, etc.) and a bone consolidation procedure.

As another example, the procedure type may further specify physical properties of a medical device that will be inserted into a subject being imaged, such as a type, thickness, gauge, length, and/or shape (e.g., curvature) of the medical device to be inserted. The medical device may be a needle, a fiber optic cable, a rod, a screw, or another type of implantable device or medical scope. The properties may further include a stiffness or flexibility (e.g., deformability) of the medical device, which may be determined based on a material (or materials) forming the medical device. For example, a smaller gauge needle (e.g., 14 gauge) may be thicker and stiffer than a larger gauge needle (e.g., 20 gauge). As another example, a fiber optic cable is more flexible than a steel rod. In some examples, the medical device to be inserted and some or all of its physical properties may be automatically selected based on the procedure type and/or image analysis. Additionally or alternatively, the operator may select, adjust, or otherwise input the physical properties of the medical device. The physical properties of the medical device may be used in determining a trajectory of the medical device within the subject during insertion, as will be elaborated below (e.g., at 316).

As still another example, the imaging protocol information may include x-ray tube voltage, current, and pulse-width settings for an x-ray source as well as frame rate settings and magnification for acquiring images at an x-ray detector. The x-ray detector may then generate a synchronization signal when an equilibrium condition is reached and send the synchronization signal back to a system controller. The x-ray source may wait for the synchronization signal from the detector and start generating x-rays at the synchronization signal once x-ray exposure is enabled. The workstation/image processing unit may stop current activities, initialize the acquisition and image processing modules, and wait for incoming frames. Further, in some examples, during an exposure preparation phase, a filament of the x-ray tube may be pre-heated (e.g., via applying a certain amount of voltage over the filament prior to x-ray exposure) in order to reduce an amount of time for the x-ray tube to reach the current setting. For example, the filament may be heated to a predetermined temperature that is based on the current setting such that the current setting may be rapidly reached once exposure begins.

At 304, the method 300 includes acquiring images of the subject for entry point and pathway planning. For example, before live imaging begins for performing the device insertion, oblique CBCT cross sections of the anatomy of interest may be obtained and in order to plan the entry point and pathway of the device, as will be elaborated below. In some examples, a 3D volume reconstruction may be performed from the acquired CBCT projection images.

At 306, the method 300 includes determining a device entry point and pathway based on the acquired images. When more than one medical device is to be inserted, separate entry points and pathways may be determined for each device. For example, the 3D volume may be used to identify the anatomy of interest, such as a target structure or region, and to plan the procedure by determining the entry point, the pathway (e.g., path), and structures to avoid. In some examples, the operator (or another clinician) may select, mark, or otherwise label (e.g., annotate) or indicate the target structure or region of the inserted device on the 3D volume. In other examples, the processor may automatically determine the target structure or region based on the received procedure information using computer vision. For example, the processor may identify an endobronchial lung biopsy site and present the identified site on the 3D volume for the operator to review and optionally adjust.

Further, the procedure plan may be used to determine operating parameters for acquiring the live (e.g., real-time) images during the procedure. Examples of such parameters may include, for example, a desired frame rate, a C-arm position and rotational angle, and a table position. For example, the parameters may be selected such that the path of the device, as well as the anatomy of interest, are approximately located within an imaging plane during the procedure. As another example, the processor may take into account a size and position of the subject and radiation dose considerations in determining the procedure plan.

At 308, the method 300 includes acquiring images of the subject at the desired frame rate and displaying the images in real-time. For example, the images may be acquired according to the imaging protocol received at 302 and the procedure plan determined at 306. For example, the processor may adjust the C-arm position and rotational angle and the table position to the determined positions for imaging the target structure or region via a motor controller (e.g., the motor controller 36 of FIG. 1). Image data may be processed for display and displayed on a display device (e.g., the display 42 of FIG. 1) in real-time, as each image is acquired. In some examples, the 3D model may be overlaid on the 2D real-time images and also displayed.

At 310, the method includes displaying the determined entry point and pathway for the device on the real-time images. For example, the processor may display the entry point and the pathway for the device as visual annotations on the real-time images. As used herein, the term "annotation" may refer to a precise location defined by a point (or points) in a given image, a linear (e.g., line) segment having a precise location within the image, and/or a set of continuous line segments each having a precise location within the image. Each annotation may or may not include an associated text (e.g., a label).

At 312, the method includes identifying the device during insertion via real-time image analysis. As one example, the processor may employ one or more object detection (e.g., image recognition) and segmentation algorithms to distinguish the medical device from tissue, bone, vessels, and other anatomical structures (e.g., via the segmentation module 210 of FIG. 2). For example, the segmentation algorithm(s) may employ shape or edge detection algorithms to define a boundary between the medical device and tissues, organs, and structures.

At 314, the method 300 includes localizing a distal end of the device in the real-time images. The distal end of the device comprises the most distant portion of the medical device from an attachment point or handle used by a clinician to insert the device. As a further example, the distal end of the device comprises a terminus of the device that is the first to enter the subject. For example, the distal end of a needle is the tip of the needle. As one example, the processor may locate the terminus of the segmented device according to the boundary of the medical device and identify its position within the 2D image space. Additionally or alternatively, the processor may localize the distal end of the device according to the determined entry point and pathway for the device, as the tip of the device is typically the closest to the target. In some examples, the operator may input information, such as by selecting the general region of the distal end of the device in the real-time images, in order to reduce uncertainty. In still other examples, additionally or alternatively, the processor may take into account knowledge of precedent angulation of the device. For example, the clinician may initially navigate the device in an angulation that reduces an uncertainty in the position of the distal end of the device. When the angulation is changed such that it becomes more challenging to locate the distal end of the device, the processor may use knowledge from the previous views to determine the current position of the distal end of the device.

When the processor is initially unsuccessful in locating the distal end of the device, additional approaches may be used in addition to those described above. For example, one x-ray image may be acquired at a higher radiation dose level and/or with collimation around an expected region of the distal end in order to enhance the acquired image. As another example, the system may output a message to the operator advising minimal gantry rotation in order to reduce or remove overlap between the device and the edges of imaged anatomical structures. As still another example, when the device is at an angulation where it is seen along its axis in a top-down or bottom-up view (e.g., where a needle appears as a point in the image instead of a length), the processor may temporarily discontinue virtual trajectory extrapolation and rendering until the angulation is changed.

At 316, the method 300 includes extrapolating a trajectory of the device within the subject in real-time. As one example, the processor may extrapolate or project the trajectory of the medical device within the subject using a geometric model that is stored in memory (e.g., in the trajectory prediction module 212 of FIG. 2). For example, the geometric model may employ curve fitting, such as polynomial or power series curve fitting models, to identify a curve of best fit based on the currently observed geometric curvature of the medical device as viewable (e.g., captured via the x-ray detector) in the real-time images. Further, the processor may extrapolate the curve of best fit based on a current position of the distal end of the device. For example, the distal end of the device may indicate an angle of trajectory of the medical device within the image plane. As such, the current position of the distal end of the medical device and its orientation may be input into the geometric model. For example, the orientation may comprise a 2D and/or 3D position of the distal end and an angle with respect to a reference, such as the determined pathway. In some examples, the curve of best fit may be extended beyond the distal end of the medical device by a predetermined distance (e.g., length). For example, the predetermined distance may be selected by the operator or pre-programmed according to the selected procedure in order to be consistent in scale with the magnification and acquired angle of the real-time images. For example, the imaging system angle with respect to the device may make a given length appear shorter or longer in the real-time images. As another example, the curve of best fit may be extended to the targeted structure or region. Further, it may be understood that the extrapolated trajectory may be updated in real-time as the medical device is further inserted or the angle of its trajectory changes.

In some examples, a relatively small portion of the medical device may be viewable in the real-time images as the medical device is initially inserted, but the viewable (e.g., captured) portion may increase as the device is further inserted. As an example, the processor may use only the viewable portion of the medical device in extrapolating the real-time trajectory of the device. In other examples, the processor may take into account a known full length and known geometry of the device in determining the trajectory.

For example, a 0.5 centimeter (cm) portion of a 14 cm linear (non-curved) needle may be viewable, and the processor may extrapolate the trajectory of a 14 cm linear needle. The extrapolation may be less accurate when only the viewable portion is considered instead of the medical device as a whole. As such, inputting or programming physical properties of the medical device for the given procedure (e.g., at 302) may help increase the accuracy of the extrapolation.

Further still, in some examples, a mechanical model may be used in addition to the geometric model. The mechanical model may take into account the physical properties of the medical device (e.g., the length, thickness, and relative stiffness) as well as physical properties (e.g., relative stiffness or flexibility) of the tissue, bone, or other anatomical structures penetrated by the medical device. As one example, the processor may identify the relative stiffness or flexibility of the tissue, bone, or other anatomical structures in part based on the procedure being performed. For example, a bone consolidation procedure may include inserting the medical device into one or more bones or bone fragments, whereas a TIPS procedure may not include inserting the medical device through bone. The processor may store a relative stiffness (or flexibility) score for each type of tissue in memory and may use these values, alone or in combination with the relative stiffness (or flexibility) of the medical device, in determining the trajectory. As an illustrative example, stiffer tissues (e.g., bone) may constrain movement of the medical device, whereas more flexible tissues (e.g., muscle) may allow for increased angular changes of the medical device during insertion. As another example, thick needles may not deform easily and therefore may be predicted to travel within a linear path. In contrast, a thin, flexible needle may deform and deflect from the linear path during insertion.

As such, in some examples, in addition to extrapolating the trajectory of the medical device, the processor may further determine an uncertainty in the extrapolation. In some examples, the uncertainty may be based on the geometric curvature. For example, there may be greater uncertainty in non-linear curve fits and the corresponding extrapolation relative to linear curve fits and the corresponding extrapolation. Additionally or alternatively, the processor may input one or more of the geometric curvature, the stiffness of the medical device being inserted, the tissue being navigated/penetrated, and the type of procedure being performed into an uncertainty algorithm, which may output a range of expected possible trajectories. In general, the uncertainty may decrease as the stiffness of the medical device increases, may increase with increasing distance to the distal end of the device, and may increase as a density of the punctured material decreases. As another example, the processor may compare previously predicted trajectories with respect to the current device position, in order to adapt the uncertainty accordingly. For example, if the current position is outside previously predicted uncertainty, the uncertainty may be further increased. Thus, the uncertainty may be learned per imaging session, per operator, and/or per organ basis. Data may be collected prospectively to refine uncertainty estimates in further insertions.

The uncertainty may generally follow a shape of the extrapolation, and the uncertainty, and thus the range of expected possible trajectories, may increase as a distance from the distal end of the medical device increases within the projected trajectory. For example, the uncertainty may be substantially cone-shaped for a linear projected trajectory or may curve as the projected trajectory curves. Further, the uncertainty may comprise a spatial region that is mapped to an area surrounding the extrapolated trajectory. The uncertainty may be visually expressed as the spatial region on the real-time images (e.g., the cone-shaped region with the width increasing as a distance from the device increases), a varying opacity of the extrapolated trajectory (e.g., less visible with increasing uncertainty), a change in line width or line type (e.g., dotted as the uncertainty increases), and/or color-mapped regions along the extrapolated trajectory (e.g., a first color for lower uncertainty, a second color for higher uncertainty).

At 318, the method 300 includes displaying the extrapolated trajectory of the device on the real-time images. For example, the extrapolated trajectory may be displayed as an annotation on the image alongside or overlapping with the determined pathway for the medical device (e.g., as determined at 306). As one example, the determined pathway may be displayed as a first color annotation or graphic, such as a line or curve, and the extrapolated trajectory may be displayed as a second color annotation or graphic that is different than the first color. Other properties, such as line thickness or style, may be different between the determined pathway and the extrapolated trajectory in order to distinguish one from another. Additionally or alternatively, text-based labels may be provided to indicated the determined (e.g., planned) pathway relative to the extrapolated (e.g., estimated) trajectory. In some examples, the uncertainty in the extrapolation may also be visually displayed. For example, the uncertainty may be visually represented as a cone or other shape around the extrapolated trajectory that generally widens as the distance from the distal end of the medical device, and thus the uncertainty, increases. Examples of displaying the extrapolated trajectory, with and without the uncertainty, are illustrated in FIGS. 4 and 5 and will be described below.

By displaying both the live, extrapolated trajectory and the desired trajectory on the real-time (e.g., live) images, the clinician may more easily identify corrections that will position the medical device within the planned pathway to reach the target structure or area. For example, if the extrapolated trajectory shows the medical device veering to the left of the planned pathway, the clinician may adjust an insertion angle of the medical device toward the right in order to bring the extrapolated trajectory closer to the planned pathway. The clinician may continue to make gradual adjustments until the extrapolated trajectory substantially overlaps with the planned pathway, for example. In contrast, without real-time feedback to show the effect of the adjustments on the extrapolated trajectory relative to the planned pathway, the clinician may under-correct or over-correct the insertion angle, resulting in less accurate placement of the medical device.

At 320, the method 300 includes determining if the acquisition is completed. For example, the acquisition may be completed when all of the prescribed view angles are obtained for the current interventional imaging procedure and imaging protocol. As another example, the operator may indicate that the acquisition is completed via an input.

If the acquisition is not completed, the method 300 returns to 308 to continue acquiring the images of the subject at the desired frame rate and displaying the images in real-time. As such, the trajectory of the device will continue to be tracked, and adjustments to the trajectory, such as due to the clinician adjusting the insertion angle, will also be determined and updated in real-time to provide feedback to the clinician.

If the acquisition is completed, the method 300 proceeds to 322 and includes stopping acquiring images of the subject. For example, the x-ray source may be deactivated, such as by discontinuing the power supply to the x-ray generator or placing the x-ray source into a lower power "stand-by" mode where the x-ray source is not actively generating x-rays until the imaging system is powered off. Further, in some examples, the x-ray detector may be unpowered or placed in a "stand-by" mode where power consumption is reduced and the x-ray detector is not actively generating electrical signals until the imaging system is powered off. The method 300 may then end. For example, the x-ray source may not be activated until the operator selects a new imaging protocol or provides another input to begin a new imaging sequence.

In this way, a live, real-time trajectory of a medical device may be displayed during an interventional imaging procedure. By displaying the live trajectory, a placement accuracy of the medical device may be increased. Further, due to the real-time guidance in an augmented reality format, a clinician may have an easier time placing the device. Overall, a length of the procedure may be decreased, which may reduce a radiation dose provided to a patient and increase patient comfort.

Turning now to FIG. 4, a first example of displaying a live estimated trajectory during insertion of a medical device is shown. In particular, FIG. 4 shows a live displayed image 400, which may be displayed to a clinician performing the insertion via a display device (e.g., the display 42). The displayed image 400 includes a live x-ray image 401 and trajectory annotations, which will be described below. For example, the trajectory annotations are overlaid on the live x-ray image 401, which may be generated from raw x-ray image data, during real-time image processing and analysis. Further, the live x-ray image 401 may be acquired using a fluoroscopic imaging system, such as the imaging system 10 of FIG. 1. It may be understood that although one live displayed image is shown, the live displayed image 400 represents one annotated x-ray image of a sequence of x-ray images that are acquired at a programmed frame rate, processed, and displayed in real-time.

The live displayed image 400 shows a needle 402 having a localized distal end 404. The distal end 404 is visually represented by an "X" in the present example, but in other examples, the distal end 404 may not be visually annotated on the live displayed image 400. The live displayed image 400 also shows a planned trajectory 406 (e.g., the determined pathway described with respect to 306 of FIG. 3) and a live estimated trajectory 408 (e.g., the extrapolated trajectory described with respect to FIG. 3). In the example shown, the live displayed image 400 uses different line types and text labels for distinguishing the planned trajectory 406 from the live estimated trajectory 408, although other examples may visually distinguish the planned trajectory 406 from the live estimated trajectory 408 in different ways. Further, in the present example, the live estimated trajectory 408 is substantially parallel to but spaced apart from the planned trajectory 406. Because the live estimated trajectory 408 does not overlap with the planned trajectory 406, the live displayed image 400 may inform the clinician to adjust the angulation of the needle 402 toward the planned trajectory 406.

FIG. 5 shows a second example of displaying a live estimated trajectory during insertion of a medical device. In particular, FIG. 5 shows a live displayed image 500, which may be displayed to a clinician performing the insertion via a display device (e.g., the display 42). The displayed image 500 includes a live x-ray image 501 and trajectory annotations, which will be described below. As described above with respect to FIG. 4, the trajectory annotations are overlaid on the live x-ray image 501, which may be acquired using a fluoroscopic imaging system (e.g., the imaging system 10 of FIG. 1), and the live displayed image 500 represents one annotated x-ray image in a sequence of x-ray images that are acquired at a programmed frame rate, processed, and displayed in real-time.

The live displayed image 500 shows a medical device 502 having a localized distal end 504. In the example shown, the medical device 502 is a fiber optic scope having a camera and a needle tip for puncturing a nodule. The distal end 504 of the medical device 502 (e.g., the needle tip) is not specifically annotated on the live displayed image 500 in the present example. The live displayed image 500 also shows a target region 503, a planned trajectory 506 for reaching the target region 503 (e.g., the determined pathway described with respect to 306 of FIG. 3), and a live estimated trajectory 508 (e.g., the extrapolated trajectory described with respect to FIG. 3). In the example shown, the live displayed image 500 uses different line for distinguishing the planned trajectory 506 from the live estimated trajectory 508. Further, in the present example, an uncertainty in the live estimated trajectory 508 is indicated by a region 510 that surrounds the live estimated trajectory 508. For example, because the medical device 502 is flexible, the medical device 502 may deviate from the live estimated trajectory 508 if the current trajectory is maintained but is expected to stay within the region 510. Even though the live estimated trajectory 508 does not overlap with the planned trajectory 506, the live displayed image 500 shows that the medical device 502 is directed toward the target region 503. As such, the clinician may make smaller adjustments to the angulation of the medical device 502 to reach the target region 503 rather than fully overlap with the planned trajectory 506. If only the planned trajectory 506, and not the live estimated trajectory 508, were shown, the clinician may instead overcorrect toward the planned trajectory 506, as it may be difficult for the clinician to anticipate whether or not the medical device 502 would reach the target region 503 while deviating from the planned trajectory 506.

In this way, the medical device may be more easily and accurately placed. As a result, an amount of time it takes to perform the procedure may be reduced, enabling the clinician to treat more patients in a day and freeing up the procedure room. Further, each patient may reach a recovery room more quickly, which may increase patient comfort.

The technical effect of extrapolating a live trajectory of a medical device during insertion within a patient from real-time images acquired during the insertion is that the medical device may be accurately placed more quickly.

The disclosure also provides support for a method for an interventional imaging procedure, comprising: identifying a medical device during insertion of the medical device within a subject based on live images of the insertion, extrapolating a trajectory of the medical device during the insertion in real-time based on the live images of the insertion, and displaying the extrapolated trajectory of the medical device on the live images. In a first example of the method, displaying the extrapolated trajectory of the medical device on the live images comprises extending the extrapolated trajectory from a distal end of the medical device as a linear or curved extrapolation. In a second example of the method, optionally including the first example, extrapolating the trajectory of the medical device during the insertion in real-time based on the live images of the insertion comprises: localizing a distal end of the medical device, and extrapolating the trajectory of the medical device based on a current position of the distal end and a geometric curvature of the medical device. In a third example of the method, optionally including one or both of the first and second examples, the method further comprises: determining the geometric curvature by identifying a curve of best fit for the medical device based on a viewable portion of the medical device in the live images, and wherein extrapolating the trajectory of the medical device further comprises extending the curve of best fit beyond the distal end of the medical device. In a fourth example of the method, optionally including one or more or each of the first through third examples, the geometric curvature of the medical device is determined based on a known length and shape of the medical device. In a fifth example of the method, optionally including one or more or each of the first through fourth examples, extrapolating the trajectory of the medical device is further based on a mechanical model of the insertion. In a sixth example of the method, optionally including one or more or each of the first through fifth examples, the mechanical model of the insertion uses one or more physical properties of the medical device to estimate deformation of the medical device during the insertion. In a seventh example of the method, optionally including one or more or each of the first through sixth examples, the one or more physical properties include at least one of a length, a thickness, and a stiffness of the medical device. In an eighth example of the method, optionally including one or more or each of the first through seventh examples, the mechanical model of the insertion uses one or more physical properties of an anatomical structure of the subject that is penetrated by the medical device during the insertion. In a ninth example of the method, optionally including one or more or each of the first through eighth examples, the method further comprises: determining an uncertainty in the extrapolated trajectory, mapping the uncertainty to a spatial region surrounding the extrapolated trajectory, and displaying the uncertainty on the live images as the spatial region. In a tenth example of the method, optionally including one or more or each of the first through ninth examples, determining the uncertainty in the extrapolated trajectory is based on one or more of a geometric curvature of the medical device, a stiffness of the medical device, a tissue the medical device is penetrating, and a type of the interventional imaging procedure.

The disclosure also provides support for a method for interventional imaging, comprising: determining a desired trajectory for insertion of a medical device within a subject based on images of the subject acquired prior to the insertion, acquiring real-time images of the subject during the insertion, displaying the desired trajectory for the insertion on the real-time images of the subject during the insertion, estimating a live trajectory of the medical device during the insertion in real-time, and displaying the live trajectory of the medical device on the real-time images of the subject. In a first example of the method, estimating the live trajectory of the medical device during the insertion in real-time comprises: identifying the medical device in the real-time images via a segmentation algorithm, determining a position of a distal end of the medical device, determining a geometric curvature of the medical device, and estimating the live trajectory of the medical device based on the geometric curvature and the position of the distal end. In a second example of the method, optionally including the first example, displaying the live trajectory of the medical device on the real-time images of the subject comprises extending the live trajectory beyond the distal end of the medical device by a pre-determined distance. In a third example of the method, optionally including one or both of the first and second examples, estimating the live trajectory of the medical device is further based on at least one of a length of the medical device, a thickness of the medical device, a stiffness of the medical device, a procedure type of the interventional imaging, and a stiffness of anatomical features being penetrated by the medical device. In a fourth example of the method, optionally including one or more or each of the first through third examples, the method further comprises: estimating an uncertainty in the live trajectory based on at least one of a shape of the live trajectory, a length of the medical device, a thickness of the medical device, a stiffness of the medical device, a procedure type of the interventional imaging, and a stiffness of anatomical features being penetrated by the medical device, and displaying a visual representation of the uncertainty on the real-time images.

The disclosure also provides support for an imaging system, comprising: a radiation source configured to project a beam of radiation toward a subject, a radiation detector configured to receive the beam of radiation projected by the radiation source and impinged by the subject, a display, and a processor operatively coupled to a memory storing instructions that, when executed, cause the processor to: acquire, via the radiation detector, live images of a medical device penetrating the subject, analyze the live images in real-time to identify the medical device and estimate a live trajectory of the medical device, and display, via the display, the live trajectory on the live images in real-time. In a first example of the system, to analyze the live images in real-time to identify the medical device and estimate the live trajectory of the medical device, the memory includes further instructions that, when executed by the processor, causes the processor to: identify the medical device via a segmentation algorithm, locate a distal end of the medical device, and estimate the live trajectory of the medical device based on a current position of the distal end and a geometric model of the medical device. In a second example of the system, optionally including the first example, to analyze the live images in real-time to estimate the live trajectory of the medical device, the memory includes further instructions that, when executed by the processor, causes the processor to: estimate the live trajectory of the medical device further based on at least one of a stiffness, a thickness, and a length of the medical device. In a third example of the system, optionally including one or both of the first and second examples, the geometric model of the medical device identifies a curve of best fit based on a curvature of the medical device, and the memory includes further instructions that, when executed by the processor, causes the processor to: estimate an uncertainty in the live trajectory of the medical device based on based on at least one of a stiffness, a thickness, and a length of the medical device, and display, via the display, the uncertainty in the live trajectory on the live images in real-time.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first,"

"second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an interventional imaging procedure, comprising:
   identifying a medical device during insertion of the medical device within a subject based on live images of the insertion;
   extrapolating a trajectory of the medical device during the insertion in real-time based on the live images of the insertion, wherein extrapolating the trajectory of the medical device comprises extending a predetermined distance beyond a distal end, the predetermined distance selected according to a selected procedure to be consistent in scale with a magnification and acquired angle of the live images; and
   displaying the extrapolated trajectory of the medical device on the live images.

2. The method of claim 1, wherein displaying the extrapolated trajectory of the medical device on the live images of the insertion comprises extending the extrapolated trajectory from the distal end of the medical device as a curved extrapolation, wherein extrapolating the trajectory of the medical device is further based on a geometric model and a mechanical model, wherein the geometric model is based on an orientation of the medical device, and wherein the mechanical model is based on physical properties of the medical device and physical properties of a tissue the medical device is penetrating.

3. The method of claim 1, wherein extrapolating the trajectory of the medical device during the insertion in real-time based on the live images of the insertion comprises:
   localizing the distal end of the medical device; and
   extrapolating the trajectory of the medical device based on a current position of the distal end and a geometric curvature of the medical device, wherein the current position of the distal end of the medical device is input into the geometric model.

4. The method of claim 3, further comprising determining the geometric curvature by identifying a curve of best fit for the medical device via the geometric model based on a viewable portion of the medical device in the live images of the insertion, wherein extrapolating the trajectory of the medical device further comprises extending the curve of best fit beyond the distal end of the medical device, and wherein the curve of best fit is extended the predetermined distance beyond the distal end, the predetermined distance selected according to the selected procedure to be consistent in scale with the magnification and acquired angle of the live images.

5. The method of claim 3, wherein the geometric curvature of the medical device is determined based on a known length and shape of the medical device.

6. The method of claim 1, wherein the mechanical model of the insertion uses one or more physical properties of the medical device to estimate deformation of the medical device during the insertion, and wherein the medical device includes a non-curved needle at the distal end of the medical device.

7. The method of claim 6, wherein the one or more physical properties include at least one of a length, a thickness, or a stiffness of the medical device.

8. The method of claim 1, wherein the mechanical model of the insertion uses one or more physical properties of an anatomical structure of the subject that is penetrated by the medical device during the insertion.

9. The method of claim 1, further comprising:
   determining an uncertainty in the extrapolated trajectory;
   mapping the uncertainty to a spatial region surrounding the extrapolated trajectory; and
   displaying the uncertainty on the live images of the insertion as the spatial region.

10. The method of claim 9, wherein determining the uncertainty in the extrapolated trajectory is based on one or more of a geometric curvature of the medical device, a stiffness of the medical device, and a type of the interventional imaging procedure.

11. A method for interventional imaging, comprising:
   determining a desired trajectory for insertion of a medical device within a subject based on images of the subject acquired prior to the insertion;
   acquiring real-time images of the subject during the insertion;
   displaying the desired trajectory for the insertion on the real-time images of the subject during the insertion;
   estimating a live trajectory of the medical device during the insertion in real-time based on the live images of the insertion, a geometric model, and a mechanical model, wherein the geometric model is based on an orientation of the medical device, wherein the orientation comprises both a position of a distal end of the medical device and an angle with respect to a reference, wherein the reference is the desired trajectory for the medical device that is separate from the live trajectory, and wherein the mechanical model is based on physical properties of the medical device and physical properties of a tissue the medical device is penetrating;
   displaying the live trajectory of the medical device on the real-time images of the subject;
   estimating an uncertainty in the live trajectory based on at least one of a shape of the live trajectory, a length of the medical device, a thickness of the medical device, a stiffness of the medical device, a procedure type of the interventional imaging, or a stiffness of anatomical features being penetrated by the medical device; and
   displaying a visual representation of the uncertainty on the real-time images of the subject.

12. The method of claim 11, wherein estimating the live trajectory of the medical device during the insertion in real-time comprises:
   identifying the medical device in the real-time images of the subject via a segmentation algorithm;
   determining a position of the distal end of the medical device;
   determining a geometric curvature of the medical device; and
   estimating the live trajectory of the medical device using the geometric model based on the geometric curvature and the position of the distal end of the medical device.

13. The method of claim 12, wherein displaying the live trajectory of the medical device on the real-time images of the subject comprises extending the live trajectory beyond the distal end of the medical device by a pre-determined distance.

14. The method of claim 12, wherein the mechanical model takes into account at least one of a length of the medical device, a thickness of the medical device, a stiffness of the medical device, a procedure type of the interventional imaging, or a stiffness of anatomical features being penetrated by the medical device.

15. An imaging system, comprising:
a radiation source configured to project a beam of radiation toward a subject;
a radiation detector configured to receive the beam of radiation projected by the radiation source and impinged by the subject;
a display; and
a processor operatively coupled to a memory storing instructions that, when executed, cause the processor to:
acquire, via the radiation detector, live images of a medical device penetrating the subject;
analyze the live images in real-time to identify the medical device and estimate a live trajectory of the medical device, the live trajectory of the medical device further estimated based on a geometric model and a mechanical model, wherein the geometric model is based on an orientation of the medical device, wherein the mechanical model is based on physical properties of the medical device and physical properties of a tissue penetrated by the medical device, and wherein estimating the live trajectory of the medical device comprises extending a predetermined distance beyond a distal end, the predetermined distance selected according to a selected procedure to be consistent in scale with a magnification and acquired angle of the live images; and
display, via the display, the live trajectory on the live images in real-time, the live trajectory being a non-linear curved pathway connecting the medical device and a target region within the subject.

16. The imaging system of claim 15, wherein to analyze the live images in real-time to identify the medical device and estimate the live trajectory of the medical device, the memory includes further instructions that, when executed by the processor, cause the processor to:
identify the medical device via a segmentation algorithm;
locate the distal end of the medical device;
estimate the live trajectory of the medical device based on a current position of the distal end of the medical device and the geometric model;
estimate an uncertainty in the live trajectory of the medical device based on at least one of a stiffness, a thickness, or a length of the medical device using the mechanical model; and
display, via the display, the uncertainty in the live trajectory on the live images in real-time.

17. The imaging system of claim 16, wherein to analyze the live images in real-time to estimate the live trajectory of the medical device, the memory includes further instructions that, when executed by the processor, cause the processor to:
estimate the live trajectory of the medical device further using the mechanical model based on at least one of a stiffness, a thickness, or a length of the medical device.

18. The imaging system of claim 16, wherein the geometric model of the medical device identifies a curve of best fit based on a curvature of the medical device.

19. A method for an interventional imaging procedure, comprising:
identifying a medical device during insertion of the medical device within a subject based on live images of the insertion;
extrapolating a trajectory of the medical device during the insertion in real-time based on the live images of the insertion, a geometric model, and a mechanical model, wherein the geometric model is based on an orientation of the medical device, and wherein the mechanical model is based on physical properties of the medical device and physical properties of a tissue the medical device is penetrating; and
displaying the extrapolated trajectory of the medical device on the live images of the insertion, wherein the orientation comprises both a position of a distal end of the medical device and an angle with respect to a reference, and wherein the reference is a determined pathway for the medical device that is separate from the extrapolated trajectory.

* * * * *